(12) United States Patent
Brazer et al.

(10) Patent No.: US 11,801,319 B2
(45) Date of Patent: Oct. 31, 2023

(54) PERSONAL ULTRAVIOLET LIGHT SANITATION DEVICE

(71) Applicant: The Innovative Lifestyle LLC, St. Louis, MO (US)

(72) Inventors: Jonathan Brazer, Pevely, MO (US); Reese Thompson, New Waterford, OH (US); Michael Hill, St. Louis, MO (US)

(73) Assignee: The Innovative Lifestyle LLC, St. Louis, MO (US)

( * ) Notice: Subject to any disclaimer, the term of this patent is extended or adjusted under 35 U.S.C. 154(b) by 285 days.

(21) Appl. No.: 17/232,930

(22) Filed: Apr. 16, 2021

(65) Prior Publication Data
US 2021/0322598 A1 Oct. 21, 2021

Related U.S. Application Data

(60) Provisional application No. 63/011,099, filed on Apr. 16, 2020.

(51) Int. Cl.
*A61L 2/10* (2006.01)
*H04M 1/02* (2006.01)
*H05B 45/38* (2020.01)

(52) U.S. Cl.
CPC ............... *A61L 2/10* (2013.01); *H04M 1/026* (2013.01); *H05B 45/38* (2020.01); *A61L 2202/11* (2013.01)

(58) Field of Classification Search
CPC ....... A61L 2/10; A61L 2202/11; H05B 45/38; H04M 1/026
USPC ........................... 250/453.11, 454.11, 455.11
See application file for complete search history.

(56) References Cited

U.S. PATENT DOCUMENTS

| 11,524,173 | B2* | 12/2022 | Stasko | ............... A61N 5/0603 |
| 2018/0169282 | A1* | 6/2018 | Kusano | ................. C01B 13/11 |
| 2021/0022676 | A1* | 1/2021 | Lamego | ............ A61B 5/02055 |

* cited by examiner

*Primary Examiner* — Nicole M Ippolito
(74) *Attorney, Agent, or Firm* — Lewis Rice LLC

(57) ABSTRACT

Systems and methods for the construction of a disinfection and/or sanitizing device that provides for individual users the ability to disinfect utilizing ultraviolet (UV) light. The device is designed to be in the form of a tool that can attach to and be readily carried in conjunction with a smart device such as a smartphone and to utilize the battery of the smart device so that it is unnecessary to obtain separate batteries.

20 Claims, 1 Drawing Sheet

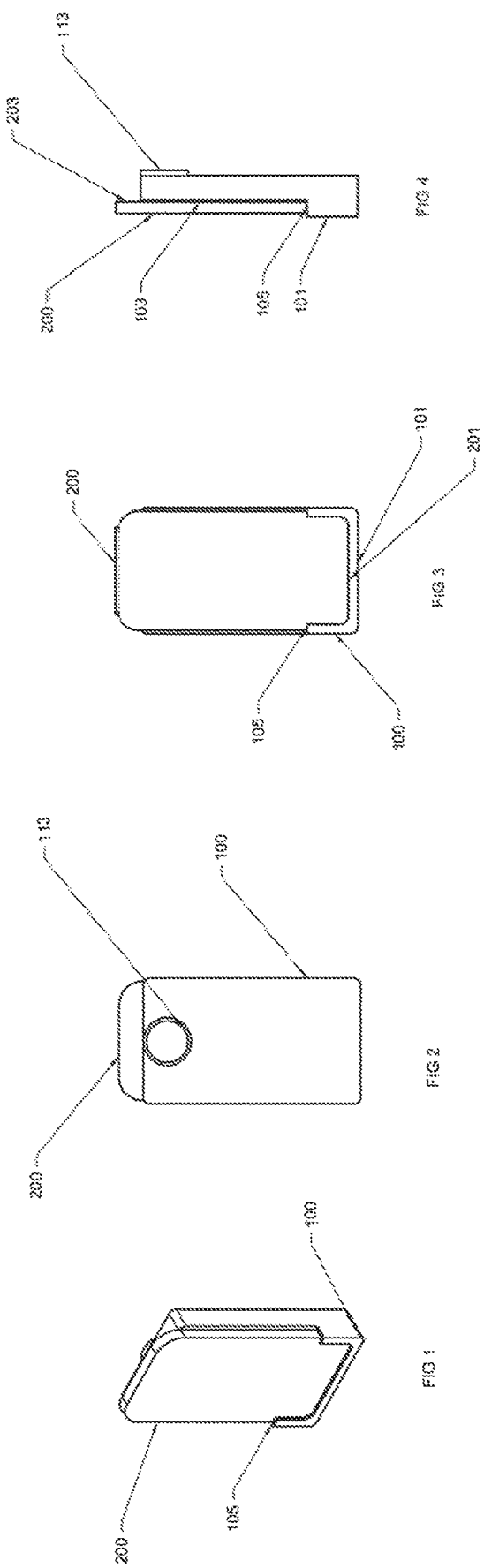

PERSONAL ULTRAVIOLET LIGHT SANITATION DEVICE

CROSS REFERENCE TO RELATED APPLICATION(S)

This application claims the benefit of U.S. Provisional Patent Application Ser. No. 63/011,099, filed Apr. 16, 2020, the entire disclosure of which is herein incorporated by reference.

BACKGROUND OF THE INVENTION

Field of the Invention

The present disclosure relates to systems and methods for providing a personal device for the disinfection or sterilization of surfaces. In particular, to a device which allows for the attachment of a UV light to a smartphone or other smart device.

Description of the Related Art

In the wake of the 2020 COVID-19 virus pandemic, the human population saw the global spread of a deadly disease leading to mass "social distancing" in an attempt to halt its spread. Social distancing was effectively a lighter form of quarantine where all individuals were intended simply to be kept at a distance from each other to avoid exponential disease spread. One of the major concerns with controlling the spread of COVID-19 was that it was not entirely clear how it was being transmitted. While it was believed that COVID-19 was primarily spread from an infected individual to others by airborne transmission, the presence of asymptomatic carriers and health privacy laws resulted in difficulties in specifically tracking distribution.

Social distancing was utilized to combat the spread of COVID-19 for many reasons, but one of the primary was that it one of the few tools that was even available. As those infected with COVID-19 were believed able to transmit the disease many days prior to exhibiting symptoms, every person was a potential carrier and there was no way to limit protective measures only to those that were infected. The virus was believed to primarily be transmitted from one to the other via infected air. Thus, respiratory guards such as surgical masks and later simple cloth face coverings became the norm to avoid viruses that may have been suspended in air from small particles expelled by one effected during a sneeze, cough, or even simple breathing. However, it was discovered relatively early on that the virus could survive on surfaces for many hours or even days depending on the nature of the surface. Hard non-porous surfaces, for example, were found to still have live viruses over a week after the surface had had any contact with an infected individual.

While virus survival on human skin was relatively limited compared to hard surface survival rates, the concern with virus survival on hard surfaces was that an infected individual could transmit the virus to a common contact surface, such as, but not limited to a door handle, via their hands shortly after the virus got on their hand from a sneeze, cough, or form the act of blowing one's nose. A later person could then touch the same surface putting the virus on their hand. That later person could then, in short succession, touch their face, and particularly their nose, which could result in virus transmission to them. It is believed that a human can touch their face 10 or even 20 times an hour so even a relatively short survival rate of the virus on human skin could result in transmission via this method.

While it is currently generally believed that COVID-19 is rarely, if at all, transferred to others via contacting common surfaces, human skin contact is often a vector for infectious disease outside of the COVID-19 virus. Specifically many microorganisms can survive on surfaces and then the skin and then be transferred to an infection point such as the mouth, nose, or an open wound by an individual touching those points of their body. Influenza, for example, along with the common cold are believed to be transmitted this way in a not insubstantial number of instances.

Another major issue with hard surface contact outside of virus transmission is the transmission of bacteria. For example *Staphylococcus* ("staph") bacteria may be transmitted to others via surfaces. Bacteria such as *E. coli* and *Salmonella* may also be transmitted via hard surfaces either to an individual directly, or to food items placed on the surface. While food preparation surfaces are typically cleaned as part of food service work, for an individual a food consumption surface (for example a public picnic table) and even some public surfaces which may encounter food may never be cleaned.

Because of the risk of surface transmission, one of the primary tools used to combat microorganism spread and infection is frequent hand washing and hand sanitizing. One of the most effective disinfection techniques for human skin is still the use of soap and water in conjunction with proper washing techniques. However, while soap and water washing for disinfection is incredibly effective, it creates concerns in that it typically requires a source of clean water (which is made dirty by the act of washing) to carry out. This leads to soap and water washing requiring substantial infrastructure to support. Effective hand washing also requires substantial time in that it must be performed for at least 20 seconds to be effective and only remains effective until the hands touch something new.

To deal with these issues, other forms of disinfection have become popular when soap and water washing may not be readily available. One product which has come into popularity recently for disinfection of human skin is alcohol-based (or other disinfectant) hand sanitizer (which is commonly referred to simply as "hand sanitizer"). While hand sanitizer can be effective, it also has problems in that it must be used for a period of time to be effective, can dry out the hands, and one must have a steady supply of it for constant use as the hands can become dirty and subject to infection transmission simply by the act of touching anything new.

To deal with the potential risk of surface transmission, disinfection of places and surfaces is common. In the early stages of the response to COVID-19, disinfection of places where those that had been found to have been infected with COVID-19 became commonplace. Further, this cleaning and disinfection continued to any place where multiple people could touch the same object and places such as large residential buildings, mass transit vehicles, and grocery stores began to rigorously clean and disinfect surfaces. This utilized everything from common disinfection and cleaning chemicals (such as chlorine bleach and ethyl alcohol), to ultraviolet (UV) light projecting robots, to heat, all the way to simple application of extended time between contacts. In many respects, social distancing, while trying to keep people from interacting to inhibit direct transmission, also served to reduce the potential viral load on any given surface by simply reducing the number of people touching it and the time between them touching it.

While increased disinfection of common surfaces likely helps reduce the possibility of surface transmission of many diseases and may be a desirable activity outside of any current pandemic, it is very difficult to actually avoid multiple people touching the same surface. While one could have products delivered to their door instead of going to a common area to avoid interacting with another person, a delivered box is still contacted by the person packing it, sorting it, and delivering it, and then can contact other boxes touched by others in the process of delivery.

To deal with this concern, many individuals have taken to disinfecting packages, groceries, and other items they obtained before they are brought into their house. The most common methods for this are either through chemical disinfection or through the application of heat. Many others also took to simply leaving boxes, deliveries, or mail outside in the sun to allow heat, natural UV light, and air currents to reduce potential microorganism load on surfaces. However, these forms of disinfection are not suitable to all products, for example, fresh foods could not be safely sprayed with chemical disinfectants and frozen food packaging cannot be readily sterilized with heat.

In addition to concerns with regards to delivered and purchased goods, another surface of potential concern was protective masks themselves. Most protective masks designed to destroy biological components are intended for single use. However, because of the lack of available surgical quality masks and the need for individuals to utilize improvised cloth masks and other forms of protective masks not necessarily designed for protection against biological threats, it became necessary to clean masks. For cloth masks, simple clothes washers could be effective. However, for masks utilizing paper filters or other non-washable materials this was often not the case and there was concern that the necessary reuse of masks could provide for a risk to the user. Decontamination of masks, and particularly for the decontamination of hard surfaces of the masks, was often simply left to time.

SUMMARY OF THE INVENTION

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, described herein are systems and methods for the construction of a disinfection and/or sanitizing device that provides for individual users the ability to disinfect utilizing ultraviolet (UV) light. The device is designed to be in the form of a tool that can to attach to and be readily carried in conjunction with a smart device such as a smartphone and to utilize the battery of the smart device so that it is unnecessary to obtain separate batteries.

There is described herein, among other things, a disinfecting tool for use with a smart device, the tool comprising: a base including a connector for electrically connecting with a battery in said smart device; a wall connected to said base and extending at least partially up a back of said smart device; an ultraviolet (UV) light source mounted in said wall; and a boost circuit, said boost circuit electrically interconnecting said battery to said UV light source to boost a voltage output of said battery to a voltage input sufficient to drive said UV light source.

In an embodiment of the tool, the smart device comprises a smartphone.

In an embodiment of the tool, the voltage output of said battery is around 3.2 volts.

In an embodiment of the tool, the voltage input is around 9 volts.

In an embodiment of the tool, the UV light source comprises a light emitting diode (LED)

In an embodiment of the tool, the UV light source emits light in an Ultraviolet C (UVC) range.

There is also described herein, in an embodiment, a device which may be used for disinfecting a surface, the device comprising: a smart device; a tool attached to said smart device, said tool including: a connector for electrically connecting with a battery in said smart device; an ultraviolet (UV) light source mounted in said wall; and a boost circuit, said boost circuit electrically interconnecting said battery to said UV light source to boost a voltage output of said battery to a voltage input sufficient to drive said UV light source.

In an embodiment of the device, the tool is attached to said smart device via a housing which at least partially encapsulates said smart device.

In an embodiment of the device, the housing comprises fitted silicon.

In an embodiment of the device, the housing comprises hard plastic.

In an embodiment of the device, the housing includes: a base including said connector; a wall including said UV light source; and two sides.

In an embodiment of the device, the tool is attached to said smart device via pressure sensitive adhesives.

In an embodiment of the device, UV light from said UV light source illuminates a space distanced said smart device.

In an embodiment of the device, UV light from said UV light source illuminates at least a portion of said smart device.

In an embodiment of the device, the smart device comprises a smartphone.

In an embodiment of the device, the voltage output of said battery is around 3.2 volts.

In an embodiment of the device, the voltage input is around 9 volts.

In an embodiment of the device, the UV light source comprises a light emitting diode (LED)

In an embodiment of the device, the UV light source emits light in an Ultraviolet C (UVC) range.

In an embodiment, the device further includes an additional battery electrically connected to said UV light source.

BRIEF DESCRIPTION OF THE DRAWINGS

FIG. 1 provides a perspective view of an embodiment of a personal ultraviolet light sanitation device attached to the back of a smart device.

FIG. 2 provides a back view of the embodiment of FIG. 1.

FIG. 3 provides a front view of the embodiment of FIG. 1.

FIG. 4 provides a side view of the embodiment of FIG. 1.

DETAILED DESCRIPTION OF PREFERRED EMBODIMENTS

It should be recognized that terms such as "disinfected", "sanitized", "cleaned", and "sterilized" typically have slightly different meanings from each other and often specify how "clean" something is based on the survival rates of certain organisms (and particularly microorganisms) of interest through the process. In the present disclosure, those terms are used interchangeably and are not intended to mean any particular level of pathogen or microorganism reduction. This is because it should be recognized that no form of sanitization or sterilization is perfect. Thus, when the present disclosure refers to a surface or area as "disinfected" or "sanitized", for example, it does not mean that there are no organisms which could cause infection present. Instead, the systems and methods proposed herein are designed to reduce the incidence of infection from a disinfected area.

The term "computer" describes hardware which generally implements functionality provided by digital computing technology, particularly computing functionality associated with microprocessors. The term "computer" is not intended to be limited to any specific type of computing device, but it is intended to be inclusive of all computational devices including, but not limited to: processing devices, microprocessors, personal computers, desktop computers, laptop computers, workstations, terminals, servers, clients, portable computers, handheld computers, cell phones, mobile phones, smartphones, tablet computers, server farms, hardware appliances, minicomputers, mainframe computers, video game consoles, handheld video game products, and wearable computing devices including, but not limited to eyewear, wristwear, pendants, fabrics, and clip-on devices.

As used herein, a "computer" is necessarily an abstraction of the functionality provided by a single computer device outfitted with the hardware and accessories typical of computers in a particular role. By way of example and not limitation, the term "computer" in reference to a laptop computer would be understood by one of ordinary skill in the art to include the functionality provided by pointer-based input devices, such as a mouse or track pad, whereas the term "computer" used in reference to an enterprise-class server would be understood by one of ordinary skill in the art to include the functionality provided by redundant systems, such as RAID drives and dual power supplies.

Those of ordinary skill in the art also appreciate that some devices which are not conventionally thought of as "computers," nevertheless exhibit the characteristics of a "computer" in certain contexts. Where such a device is performing the functions of a "computer" as described herein, the term "computer" includes such devices to that extent. Devices of this type include, but are not limited to: network hardware, print servers, file servers, NAS and SAN, load balancers, and any other hardware capable of interacting with the systems and methods described herein in the matter of a conventional "computer."

Throughout this disclosure, the term "software" refers to code objects, program logic, command structures, data structures and definitions, source code, executable and/or binary files, machine code, object code, compiled libraries, implementations, algorithms, libraries, or any instruction or set of instructions capable of being executed by a computer processor, or capable of being converted into a form capable of being executed by a computer processor, including, without limitation, virtual processors, or by the use of run-time environments, virtual machines, and/or interpreters. Those of ordinary skill in the art recognize that software can be wired or embedded into hardware, including, without limitation, onto a microchip, and still be considered "software" within the meaning of this disclosure. For purposes of this disclosure, software includes, without limitation: instructions stored or storable in hard drives, RAM, ROM, flash memory BIOS, CMOS, mother and daughter board circuitry, hardware controllers, USB controllers or hosts, peripheral devices and controllers, video cards, audio controllers, network cards, Bluetooth® and other wireless communication devices, virtual memory, storage devices and associated controllers, firmware, and device drivers. The systems and methods described here are contemplated to use computers and computer software typically stored in a computer- or machine-readable storage medium or memory.

Throughout this disclosure, the term "network" generally refers to a voice, data, or other telecommunications network over which computers communicate with each other. The term "server" generally refers to a computer providing a service over a network, and a "client" generally refers to a computer accessing or using a service provided by a server over a network. Those having ordinary skill in the art will appreciate that the terms "server" and "client" may refer to hardware, software, and/or a combination of hardware and software, depending on context. Those having ordinary skill in the art will further appreciate that the terms "server" and "client" may refer to endpoints of a network communication or network connection, including, but not necessarily limited to, a network socket connection. Those having ordinary skill in the art will further appreciate that a "server" may comprise a plurality of software and/or hardware servers delivering a service or set of services. Those having ordinary skill in the art will further appreciate that the term "host" may, in noun form, refer to an endpoint of a network communication or network (e.g., "a remote host"), or may, in verb form, refer to a server providing a service over a network ("hosts a website"), or an access point for a service over a network.

Throughout this disclosure, the term "transmitter" refers to equipment, or a set of equipment, having the hardware, circuitry, and/or software to generate and transmit electromagnetic waves carrying messages, signals, data, or other information. A transmitter may also comprise the componentry to receive electric signals containing such messages, signals, data, or other information, and convert them to such electromagnetic waves. The term "receiver" refers to equipment, or a set of equipment, having the hardware, circuitry, and/or software to receive such transmitted electromagnetic waves and convert them into signals, usually electrical, from which the message, signal, data, or other information may be extracted. The term "transceiver" generally refers to a device or system that comprises both a transmitter and receiver, such as, but not necessarily limited to, a two-way radio, or wireless networking router or access point. For purposes of this disclosure, all three terms should be understood as interchangeable unless otherwise indicated; for example, the term "transmitter" should be understood to imply the presence of a receiver, and the term "receiver" should be understood to imply the presence of a transmitter.

For purposes of this disclosure, there will also be significant discussion of a special type of computer referred to as a "mobile communication device" or simply "smart device". A mobile communication device may be, but is not limited to, a cellular phone, a smartphone, tablet PC, e-reader, satellite navigation system ("SatNav"), fitness device (e.g. a Fitbit™ or Jawbone™) or any other type of mobile computer, whether of general or specific purpose functionality. Generally speaking, a mobile communication device is network-enabled and communicating with a server system providing services over a telecommunication or other infrastructure network. A mobile communication device is essentially a mobile computer, but one which is commonly not associated with any particular location, is also commonly carried on a user's person, and usually is in near-constant real-time communication with a network. A mobile communication device will almost always include its own power supply which is commonly in the form of a rechargeable battery.

FIGS. 1-4 provide for various images of an embodiment of an ultraviolet (UV) light disinfecting tool (100) that is designed to attach to any common form of smart device (200) and particularly a cell phone or smartphone. The disinfecting tool (100) can attach to any smart device (200) and, thus, be with individuals everywhere they go. It is small, convenient, and efficient disinfection method using UV light disinfection which is expected to have a germ-killing rate as high as 99.9% of bacteria and viruses. Additionally, UV disinfection results in no chemical residue left behind and can be used on textiles, frozen and refrigerated items, most fresh foods, and on materials having uneven or complex surfaces that light can still reach while water may not.

The embodiment of the disinfecting tool (100) shown in FIGS. 1-4 is typically sized and shaped to be able to readily attach to a smart device (200) in the form of a smartphone. It will typically comprise a housing including a base (101) which is designed to fit under the base (201) of the smart device (200). While which surface is the base (201) is somewhat subjective depending on the nature of the smart device (201), the base (201) as used herein will typically be the location of a charging and/or data port (not shown) of the smart device (200). The base (101) will include a connector which will interface with that port and allow for electrical transfer between the connector and the port interconnecting the smart device (200) and disinfecting tool (100) electrically. Data may also be shared between the smart device (200) and disinfecting tool (100) in an embodiment, but that is not required.

The disinfecting tool (100) housing will also typically include a wall (103) which will generally be positioned to be flush against the back (203) of the smart device (200). The wall (103) includes a UV light source (113). The wall (103) may extend just part way up the back (203) of the smart device (200) as shown, or may extend further possibly ending in a top that goes over the top (207) of the smart device (200). The wall (103) may include cutouts (as necessary) to allow for the smart device's camera, buttons, other ports, or other devices to not be blocked by the structure of the wall (103).

The disinfecting tool (100) housing may also include one or two partial sides (105) which extend along the side of the smart device (200). The partial sides (105) and wall (103) will typically serve to stabilize the disinfecting tool (100) against the smart device (200) to make the two items behave as a single unit. To support this operation, the various components (101), (103) and (105) of the disinfecting tool (100) may be sized and shaped to allow for a "clip-type" connection with the smart device (200) where the smart device (200) fits snugly via friction into the disinfecting tool (100).

The disinfecting tool (100), however, may connect to the smart device via alternative or additional systems and means instead of or in addition to using a housing which will allow for the disinfecting tool (100) to be mounted securely to the smart device (200) and the choice of system or means for connection may also depend on the specific nature of the smart device (200) and it's size and shape. Some systems and/or means which may be used include, but not limited to, pressure sensitive adhesives, clamping mechanisms, or fitted silicon and hard plastic casings.

The disinfecting tool (100) in typical operation draws power from the battery of the smart device (200). The UV source (113) may, however, require additional power compared that which can be directly drawn for the smart device (200) battery. The device may take the power (Voltage× Current=Power) available and boost it to operate the UV source (113) at the proper wavelength and power levels to disinfect and sanitize bacterial, germicidal, and viral inhabited surfaces.

The UV source (113) shall generally be electrically connected directly to the smart device (200) by means of proper adaptation to the charging port utilized for the DC power source, typically a battery, contained within and used to operate the smart device (200). The DC power source, generally consisting of a 3.2 volt power supply will then be converted via a boost converter circuit to the desired power levels to operate the UV source (113), typically 9 volts. The disinfecting tool (100) may also or additionally include its own battery or capacitor separate from the smart device (200) battery to provide an additional or alternative source of power. It may also include an alternative power source such as, but not limited to, a solar collector, kinetic energy scavenger, or combination thereof.

The UV source (113) will typically comprise a light emitting diode (LED) or similar source preferably operating in the Ultraviolet C (UVC) range of about 180 nm to about 280 nm which is believed to minimize the risk of safety effects of skin and eye irritation of the user. However, alternative wavelengths of UV light, or in fact light in other electromagnetic spectrums, may be used based on their disinfection properties and the nature of target organisms to be destroyed by the UV source (113).

While the UV source (113) in the FIGS is also shown as aimed to provide light away from the back (203) of the smart device (200), it should be recognized that the UV light alternatively or additionally be aimed to bathe the smart device (200) itself. For example, part of the UV light from UV source (113) may be directed or reflected around other parts of the smart device (200) such as to disinfect a touchscreen, mouthpiece, earpiece, or other components of the smart device (200).

The disinfecting tool (100), in an embodiment, may also contain additional ports for further connectivity. For example, the disinfecting tool (100) may include an additional power-in port to attach to another external DC power source that may operate the disinfecting tool (100) while attached to the smart device (200). This could help extend the operational life of disinfecting tool (100) or reduce the speed of power drain on the smart device (200) for using disinfecting tool (100). The disinfecting tool (100) may also or alternatively include a charge port to attach to another DC power source that may be used to re-charge the attached smart device (200) while also operating the disinfecting tool (100). The disinfecting tool (100) may also contain auxiliary ports to attach additional functionality (including additional devices (100) operating off of the boosted power levels of the disinfecting tool (100).

To use the disinfecting tool (100) the user would turn on the UV source (113) and hold or sweep the UV light over area to be disinfected. Reasonable disinfection can typically be completed in about 20 seconds although a user may use a longer or shorter window as desired. The control to switch the UV source (113) on and off may be, for example, via a hardware switch located on the disinfecting tool (100) or via a software application (an "app") running on the smart device (200). The disinfecting tool (101) may be used to sterilize surfaces such as, but not limited to, door knobs, utensils, seating areas, stair rails, clothing or fabrics, food items, other areas of concerns, and/or other high touch surfaces. It may also be used to protect first responders, medical staff, individuals and their family members against infection by allowing them to readily carry a UV source with them. In an embodiment, it may even be attached to a smart device (200) specifically used in medical settings (including without limitations, hospitals, doctor's offices and nursing homes) such as, but not limited to, a tablet computer (200) used by medical personnel for electronic medical records (EMR) entry or for generating digital prescriptions.

While the invention has been disclosed in conjunction with a description of certain embodiments, including those that are currently believed to be useful embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

It will further be understood that any of the ranges, values, properties, or characteristics given for any single component of the present disclosure can be used interchangeably with any ranges, values, properties, or characteristics given for any of the other components of the disclosure, where compatible, to form an embodiment having defined values for each of the components, as given herein throughout. Further, ranges provided for a genus or a category can also be applied to species within the genus or members of the category unless otherwise noted.

The qualifier "generally," and similar qualifiers as used in the present case, would be understood by one of ordinary skill in the art to accommodate recognizable attempts to conform a device to the qualified term, which may nevertheless fall short of doing so. This is because terms such as "spherical" are purely geometric constructs and no real-world component or relationship is truly "spherical" in the geometric sense. Variations from geometric and mathematical descriptions are unavoidable due to, among other things, manufacturing tolerances resulting in shape variations, defects and imperfections, non-uniform thermal expansion, and natural wear. Moreover, there exists for every object a level of magnification at which geometric and mathematical descriptors fail due to the nature of matter. One of ordinary skill would thus understand the term "generally" and relationships contemplated herein regardless of the inclusion of such qualifiers to include a range of variations from the literal geometric meaning of the term in view of these and other considerations.

The invention claimed is:

1. A disinfecting tool for use with a smart device, the tool comprising:
 a base including a connector for electrically connecting with a battery in said smart device;
 a wall connected to said base and extending at least partially up a back of said smart device;
 an ultraviolet (UV) light source mounted in said wall; and
 a boost circuit, said boost circuit electrically interconnecting said battery to said UV light source to boost a voltage output of said battery to a voltage input sufficient to drive said UV light source.

2. The tool of claim 1 wherein said smart device comprises a smartphone.

3. The tool of claim 1 wherein said voltage output of said battery is around 3.2 volts.

4. The tool of claim 3 wherein said voltage input is around 9 volts.

5. The tool of claim 1 wherein said UV light source comprises a light emitting diode (LED).

6. The tool of claim 1 wherein said UV light source emits light in an Ultraviolet C (UVC) range.

7. A device which may be used for disinfecting a surface, the device comprising:
 a smart device;
 a tool attached to said smart device, said tool including:
  a connector for electrically connecting with a battery in said smart device;
  an ultraviolet (UV) light source mounted in said wall; and
  a boost circuit, said boost circuit electrically interconnecting said battery to said UV light source to boost a voltage output of said battery to a voltage input sufficient to drive said UV light source.

8. The device of claim 7 wherein said tool is attached to said smart device via a housing which at least partially encapsulates said smart device.

9. The device of claim 8 wherein said housing comprises fitted silicon.

10. The device of claim 8 wherein said housing comprises hard plastic.

11. The device of claim 8 wherein said housing includes:
 a base including said connector;
 a wall including said UV light source; and
 two sides.

12. The device of claim 7 wherein said tool is attached to said smart device via pressure sensitive adhesives.

13. The device of claim 7 wherein UV light from said UV light source illuminates a space distanced said smart device.

14. The device of claim 7 wherein UV light from said UV light source illuminates at least a portion of said smart device.

15. The device of claim 7 wherein said smart device comprises a smartphone.

16. The device of claim 7 wherein said voltage output of said battery is around 3.2 volts.

17. The device of claim 16 wherein said voltage input is around 9 volts.

18. The device of claim 7 wherein said UV light source comprises a light emitting diode (LED).

19. The device of claim 7 wherein said UV light source emits light in an Ultraviolet C (UVC) range.

20. The device of claim 7 further including an additional battery electrically connected to said UV light source.

* * * * *